(12) United States Patent
Carim

(10) Patent No.: US 7,187,985 B2
(45) Date of Patent: Mar. 6, 2007

(54) BIOMEDICAL ELECTRODE WITH CURRENT SPREADING LAYER

(75) Inventor: Hatim M. Carim, West St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 498 days.

(21) Appl. No.: 10/623,359

(22) Filed: Jul. 18, 2003

(65) Prior Publication Data

US 2005/0015134 A1    Jan. 20, 2005

(51) Int. Cl.
*A61N 1/04* (2006.01)

(52) U.S. Cl. .................................... 607/152

(58) Field of Classification Search ............... 607/115, 607/142, 152
See application file for complete search history.

(56) References Cited

U.S. PATENT DOCUMENTS

| | | | |
|---|---|---|---|
| 4,067,342 A | 1/1978 | Burton | |
| 4,524,087 A | 6/1985 | Engel | |
| 4,539,996 A | 9/1985 | Engel | |
| 4,685,467 A | 8/1987 | Cartmell et al. | |
| 4,722,354 A | 2/1988 | Axelgaard et al. | |
| 4,727,880 A | 3/1988 | Roberts | |
| 4,748,983 A | 6/1988 | Shigeta et al. | |
| 4,771,783 A | 9/1988 | Roberts | |
| 4,776,350 A | 10/1988 | Grossman et al. | |
| 4,848,353 A | 7/1989 | Engel | |
| 4,852,571 A | 8/1989 | Gadsby et al. | |
| 4,890,622 A | 1/1990 | Ferrari | |
| 4,895,169 A | 1/1990 | Heath | |
| 4,899,754 A | 2/1990 | Bly et al. | |
| 5,133,356 A | 7/1992 | Bryan et al. | |
| 5,225,473 A | 7/1993 | Duan | |
| 5,265,579 A | 11/1993 | Ferrari | |
| 5,276,079 A | 1/1994 | Duan et al. | |
| 5,330,526 A | 7/1994 | Fincke et al. | |
| 5,338,490 A | 8/1994 | Dietz et al. | |
| 5,362,420 A | 11/1994 | Itoh et al. | |
| 5,366,497 A | 11/1994 | Ilvento et al. | |

(Continued)

FOREIGN PATENT DOCUMENTS

EP    0 983 775 A2    3/2000

(Continued)

OTHER PUBLICATIONS

"3M XYZ-Axis Electrically Conductive Tape 9713," *Technical Data*, 3M, St. Paul, Minnesota, Jun. 1999; 4 pages total.

(Continued)

*Primary Examiner*—Scott M. Getzow
(74) *Attorney, Agent, or Firm*—Daniel R. Pastirik; Kevin W. Raasch

(57) ABSTRACT

A biomedical electrode is disclosed that distributes current over the entire surface of a conductive polymeric sheet using a current spreading layer located on the upper surface of the conductive polymeric sheet (i.e., the surface facing away from the patient). The conductive polymeric sheet includes a conductive undercoating on its lower surface (i.e., the surface facing the patient). An electrolyte layer (e.g., a hydrogel pressure sensitive adhesive) is located on the bottom of the biomedical electrode, with the conductive undercoating located between the electrolyte layer and the conductive polymeric sheet. The biomedical electrode is in electrical communication with the patient's skin through the electrolyte layer.

31 Claims, 3 Drawing Sheets

U.S. PATENT DOCUMENTS

| | | |
|---|---|---|
| 5,385,679 A | 1/1995 | Uy et al. |
| 5,438,988 A | 8/1995 | Duan et al. |
| 5,506,059 A | 4/1996 | Robbins et al. |
| 5,571,165 A | 11/1996 | Ferrari |
| 5,674,561 A | 10/1997 | Dietz et al. |
| 5,733,324 A | 3/1998 | Ferrari |
| 5,785,040 A * | 7/1998 | Axelgaard ............ 600/391 |
| 5,824,033 A | 10/1998 | Ferrari |
| 5,916,244 A | 6/1999 | Walters |
| 6,023,631 A | 2/2000 | Cartmell et al. |
| 6,356,779 B1 | 3/2002 | Katzenmaier et al. |

| | | |
|---|---|---|
| 2002/0156357 A1 | 10/2002 | Axelgaard |

FOREIGN PATENT DOCUMENTS

| | | |
|---|---|---|
| WO | WO 97/24149 A1 | 7/1997 |
| WO | WO 97/24376 A1 | 7/1997 |
| WO | WO 97/24378 A1 | 7/1997 |

OTHER PUBLICATIONS

"3M XYZ-Axis Electrically Conductive Tape 9712," *Technical Data*, 3M, St. Paul, Minnesota, Aug. 2001; 4 pages total.

* cited by examiner

BIOMEDICAL ELECTRODE WITH CURRENT SPREADING LAYER

BACKGROUND

Multifunction biomedical electrodes may be used for a variety of purposes. In some instances, multifunction biomedical electrodes may be used to defibrillate patients whose heart is in a state of fibrillation and in imminent danger of death. Multifunction biomedical electrodes may also be used for external pacing of the heart. Multifunction biomedical electrodes may also be required to function as ECG (electrocardiograph) monitoring electrodes when not providing defibrillation or pacing functions.

These requirements make the design of a multifunction biomedical electrode difficult, especially when, for example, the electrodes are required to provide cardiac pacing for extended periods of time (e.g., twelve hours or more). Among the design constraints to be considered are that in, e.g., defibrillation, electrical energies of up to 360 Joules may be delivered repeatedly to a patient using the multifunction biomedical electrode. At such energy levels, currents in the range of 30 to 60 amperes in amplitude and 4–10 milliseconds duration are not uncommon.

Attempts to provide multifunction biomedical electrodes have included an electrically conductive sheet with a lead wire attached. One side of this conductor has an ionically conductive electrolyte usually in the form of a hydrogel. The conductive sheet is typically a metal foil (e.g., tin), in which case exposed strands of one end of the lead wire are anchored to the metal foil to provide a mechanical and electrical connection by means of a rivet, pressure sensitive tape, solder or electrically conductive glue (epoxy, adhesive) etc. The connection between the strands and the metal foil may be made on one of the two sides of the foil or by piercing the foil at any location. Because the metal foil is highly conductive, the location of the connection site on the foil only minimally affects the current distribution from the face of the side of the foil in contact with the electrolyte and then the skin of the patient.

One potential disadvantage of this approach is that the metal foil may reduce the effectiveness of radiological images taken through the multifunction biomedical electrode because of the shadow cast by the metal foil in any such radiological images.

To address radiological imaging issues, one approach has involved replacement of the metal foil by an electrically conductive polymeric sheet as discussed in, e.g., U.S. Pat. No. 5,571,165 to Ferrari. Multifunction biomedical electrodes with conductive polymeric sheets such as those described in U.S. Pat. No. 5,571,165 to Ferrari purportedly address issues related to irritation and burning of patients' skin around the perimeter of the electrode when used in defibrillation. However, such electrodes subjected to the passage of multiple defibrillation pulses (of, e.g., 100 to 360 Joules) exhibit hot spots of temperature rise directly under the stranded lead wire connection in the central part of the electrode.

SUMMARY OF INVENTION

The present invention provides a biomedical electrode that distributes current over the entire surface of a conductive polymeric sheet using a current spreading layer located on the upper surface of the conductive polymeric sheet (i.e., the surface facing away from the patient). The conductive polymeric sheet includes a conductive undercoating on its lower surface (i.e., the surface facing the patient). An electrolyte layer (preferably a hydrogel pressure sensitive adhesive) is located on the bottom of the biomedical electrode, with the conductive undercoating located between the electrolyte layer and the conductive polymeric sheet. The biomedical electrode is in electrical communication with the patient's skin through the electrolyte layer.

The biomedical electrodes of the present invention are preferably capable of functioning as multifunction biomedical electrodes as defined above. In other words, the biomedical electrodes of the present invention may preferably be capable of functioning as ECG monitoring electrodes for the monitoring of a patient's cardiac activity. In addition to ECG monitoring, the biomedical electrodes may also have the ability to deliver electrical energy for cardiac pacing and/defibrillation purposes. Further, the biomedical electrodes may also be useful in electrosurgical applications.

The current spreading layer may provide a number of advantages to biomedical electrodes of the present invention. For example, the current spreading layer may preferably exhibit lower electrical resistance in the x-y plane (i.e., across the upper surface of the conductive polymeric sheet) than, e.g., a conductive polymeric sheet. To do so, it may be preferred that the material or materials used for the current spreading layer exhibit a bulk conductivity that is higher than the bulk conductivity of the material or materials used to manufacture the conductive polymeric sheet. Although not being bound by theory, it is theorized that the current spreading layer preferentially distributes current over the upper surface of the conductive polymeric sheet as compared to the normal direction through the upper and lower surfaces of the conductive polymeric sheet.

The distribution of electric current over substantially the entire surface of the conductive polymeric sheet by the current spreading layer may preferably reduce or eliminate the creation of hot spots directly underneath the connection between the electrical connector (e.g., lead) and the remainder of the electrode when used to deliver significant levels of electrical energy (e.g., defibrillation pulses). By reducing or eliminating hot spots, patient comfort may be improved during use of the multifunction biomedical electrodes of the present invention.

Another manner in which hot spots may develop is that, depending on the length of service of the biomedical electrode (such as during extended cardiac pacing operation), the conductive undercoating on the lower surface of the conductive polymeric sheet may develop regions or islands of differing composition if the current being delivered to the conductive undercoating is non-uniform. The regions or islands may deliver current to the patient non-uniformly, which may result in hot spots at the electrode/patient interface. By preferentially spreading current uniformly across the conductive polymeric sheet, the current spreading layer may prevent or delay formation of such regions or islands in the conductive undercoating.

Still another manner in which hot spots and nonuniformities may develop is due to a lack of pliability in the conductive undercoating. If the biomedical electrode is flexed, the conductive undercoating may crack or otherwise be damaged such that the resistance along the conductive paths to all areas of the conductive undercoating are not equivalent. The result may be that different amounts of electrical energy may be delivered to different areas of the conductive undercoating, with hot spots potentially being generated due to the differences. The current spreading layer may, however, provide a very low resistance backplane (through the conductive polymeric sheet), causing all areas of the conductive undercoating to behave as a single conductive entity.

Another potential advantage of multifunction biomedical electrodes of the present invention is that the current spreading layer may provide the opportunity to locate an electrical connector at any point on the electrode. Because of limited electrical conductivity of the various components, electrodes such as those described in U.S. Pat. No. 5,571,165 to Ferrari typically require electrical energy to be delivered at or near the center of the electrode. Because of the low resistance (or, conversely, high conductivity) of the current spreading layer in preferred electrodes of the present invention, the electrical energy may be delivered to the electrode at any location on the current spreading layer, including near or at the edge thereof. It may even be possible to deliver electrical energy to electrodes of the present invention in a direct manner (through, e.g., a snap connector or clamp) that is in direct contact with both the current spreading layer and the conductive undercoating, thus relying on the high relative conductivity of the current spreading layer to spread current over the entire electrode.

Still another potential advantage of the multifunction biomedical electrodes of the present invention is that the current spreading layer may function as a moisture barrier to significantly reduce or prevent migration of water, salts, etc. from the conductive adhesive towards the electrical connector (e.g., lead). Such migration, if not limited, may result in corrosion at the interface between the electrical connector and the remainder of the electrode. Corrosion can reduce the shelf-life of the multifunction biomedical electrodes of the present invention and/or create hot spots during use (due to the high resistance of the corroded materials).

Yet another potential advantage of biomedical electrodes according to the present invention is that the construction may exhibit radiolucency, i.e., the biomedical electrodes may not prohibit radiological imaging of the patient through the skin on which the electrode is located. The conductive polymeric sheet with a current spreading layer on one surface and a conductive undercoating on the opposite surface may preferably be constructed so as to not prevent effective radiological imaging.

In addition, it may be preferred that the electrical connector be constructed of materials that also do not prevent effective radiological imaging. For example, the electrical connector may be provided in the form of a multi-stranded wire in which the strands are, for example, metal-coated carbon fibers or aluminum strands. In addition to using components for the conductive part of the wire that do not completely obscure radiological images, it may also be advantageous to provide the wire in a jacket that does not itself completely obscure radiological images.

In one aspect, the present invention provides a biomedical electrode that includes a conductive polymeric sheet having an upper side and a lower side; a conductive undercoating attached to the lower side of the conductive polymeric sheet; an electrolyte layer attached to the conductive undercoating, wherein the conductive undercoating is located between the electrolyte layer and the lower side of the conductive polymeric sheet; a current spreading layer attached to the upper side of the conductive polymeric sheet, wherein the current spreading layer includes a metallic layer on the upper side of the conductive polymeric sheet; and an electrical connector attached to the biomedical electrode, the electrical connector in electrical communication with the conductive polymeric sheet through the current spreading layer.

In another aspect the present invention provides a biomedical electrode including a conductive polymeric sheet having an upper side and a lower side; a conductive undercoating attached to the lower side of the conductive polymeric sheet; an electrolyte layer attached to the conductive undercoating, wherein the conductive undercoating is located between the electrolyte layer and the lower side of the conductive polymeric sheet; a current spreading layer attached to the upper side of the conductive polymeric sheet, wherein the current spreading layer is in the form of a pattern that includes one or more voids, wherein a portion of the upper side of the conductive polymeric sheet is free of the current spreading layer within the one or more voids; and an electrical connector attached to the biomedical electrode, the electrical connector in electrical communication with the conductive polymeric sheet through the current spreading layer.

In another aspect, the present invention provides a method of manufacturing a biomedical electrode by providing a conductive polymeric sheet having an upper side and a lower side; attaching a conductive undercoating to a lower side of a conductive polymeric sheet; attaching an electrolyte layer to the conductive undercoating, wherein the conductive undercoating is located between the electrolyte layer and the lower side of the conductive polymeric sheet; providing a current spreading layer on the upper side of the conductive polymeric sheet, wherein the current spreading layer includes a metallic layer on the upper side of the conductive polymeric sheet; and attaching an electrical connector to the biomedical electrode, the electrical connector in electrical communication with the conductive polymeric sheet through the current spreading layer.

In another aspect, the present invention provides a method of manufacturing a biomedical electrode by providing a conductive polymeric sheet having an upper side and a lower side; attaching a conductive undercoating to a lower side of a conductive polymeric sheet; attaching an electrolyte layer to the conductive undercoating, wherein the conductive undercoating is located between the electrolyte layer and the lower side of the conductive polymeric sheet; providing a current spreading layer on an upper side of the conductive polymeric sheet, wherein the current spreading layer is in the form of a pattern that includes one or more voids, wherein a portion of the upper side of the conductive polymeric sheet is free of the current spreading layer within the one or more voids; and attaching an electrical connector to the biomedical electrode, the electrical connector in electrical communication with the conductive polymeric sheet through the current spreading layer.

These and other features and advantages of the present invention may be described below in connection with various illustrative embodiments of the invention.

DETAILED DESCRIPTION OF ILLUSTRATIVE EMBODIMENTS OF THE INVENTION

Figure 1:
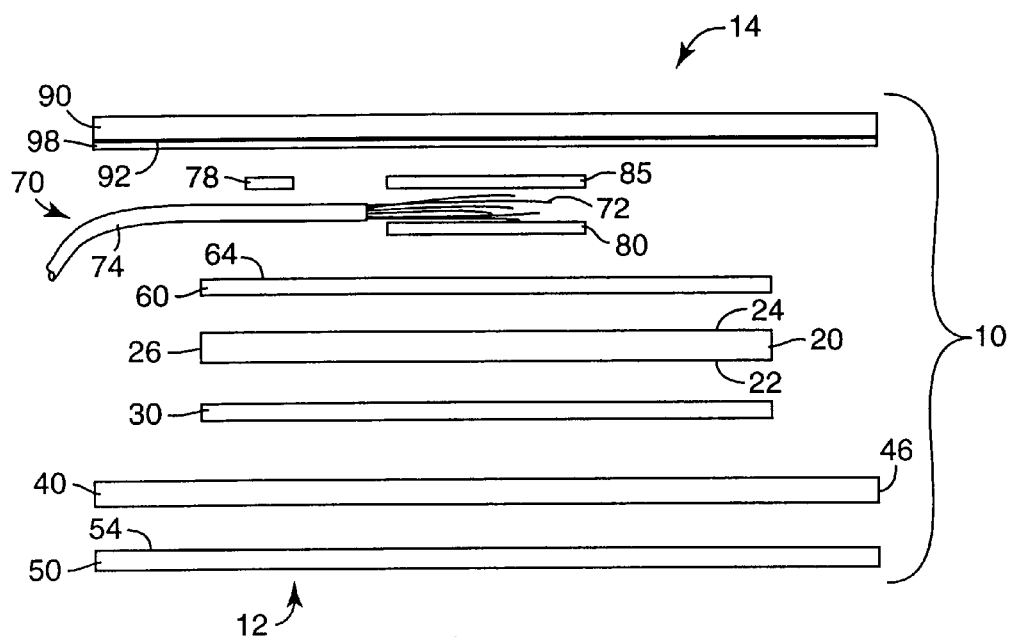
FIG. 1 is an exploded edge view of one biomedical electrode according to the present invention.

In the following detailed description of illustrative embodiments, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

FIG. 1 is an exploded edge view of one biomedical electrode 10 according to the present invention. The electrode 10 includes a lower side 12 and an upper side 14. The lower side 12 is the side that, in use, faces the patient while the upper side 14 faces away from the patient. This convention holds for the other components in the electrode 10 as well, i.e., the lower side of a component is that side of the component that faces the patient in use, while the upper side of each component faces away from the patient.

The electrode 10 includes a conductive polymeric sheet 20 having a lower side 22 and an upper side 24. The conductive polymeric sheet 20 may preferably be relatively flexible such that, alone, it could conform to the anatomy of a patient. The thickness of the conductive polymeric sheet 20 may be, e.g., as low as 20 micrometers, while on the upper end of an exemplary range, the conductive polymeric sheet 20 may be up to 500 micrometers thick.

The conductive polymeric sheet 20 may be made of intrinsically conductive polymers or nonconductive polymers made conductive by any suitable technique. For example, the sheet 20 may include electrically conductive particles and/or chemical moieties dispersed in a polymeric matrix. The polymeric matrix material may be any suitable polymer or polymers, e.g., PVC, ethyl vinyl acetate (EVA), etc. The electrically conductive particles may be, e.g., carbon black, graphite, metallic, metal-coated fibers, etc. It may be preferred that the conductive polymeric sheet 20 be radiolucent, i.e., that it not obscure underlying patient anatomy enough to prevent effective radiological imaging.

A conductive undercoating 30 is located on the lower side 22 of the conductive polymeric sheet 20. The conductive undercoating 30 preferably provides a substantially nonpolarizable interface with the electrolyte layer 40 when in use on the patient side of a biomedical electrode. Nonlimiting examples of electrically conductive materials that may be used to provide a substantially non-polarizable interface with the electrolyte layer 40 include silver metal, tin metal, alloys of tin and lead, combinations of metal-metal salts, and the like. The materials may be, e.g., provided as a foil, in an ink, or vapor deposited as described in, e.g., U.S. Pat. No. 5,506,059 (Robbins et al.). One suitable conductive undercoating 30 is an ink containing silver and silver chloride. As an ink, the conductive undercoating 30 may be applied by, e.g., printing. When provided as a silver/silver chloride ink, the conductive undercoating 30 may have a thickness in the range of, e.g., 1 micrometer to 125 micrometers, although an undercoating with a thickness outside of this range may be used if it provides the desired electrical characteristics.

The conductive undercoating 30 may, if desired, be provided in multiple layers such that a differential thickness is provided as described in, e.g., U.S. Pat. Nos. 5,571,165; 5,733,324; and 5,824,033 (all to Ferrari). The differential thickness may assist in decreasing current density along the edges of the electrode.

An ionically conductive electrolyte layer 40 is located over the conductive undercoating 30, such that the conductive undercoating 30 is located between the electrolyte layer 40 and the lower side 22 of the conductive polymeric sheet 20. The electrolyte layer 40 may preferably be hydrophilic and may preferably include a hydrogel. It may be further preferred that the electrolyte layer 40 be an ionically conductive hydrogel pressure sensitive adhesive that is biocompatible with mammalian skin. Examples of some suitable ionically conductive pressure sensitive adhesives that could potentially be used in connection with the present invention may be described in, e.g., U.S. Pat. No. 4,524,087 (Engel); U.S. Pat. No. 4,539,996 (Engel); U.S. Pat. No. 4,848,353 (Engel); U.S. Pat. No. 5,133,356 (Bryan et al.); U.S. Pat. No. 5,225,473 (Duan); U.S. Pat. No. 5,276,079 (Duan et al.); U.S. Pat. No. 5,338,490 (Dietz et al.); U.S. Pat. No. 5,362,420 (Itoh et al.); U.S. Pat. No. 5,385,679 (Uy et al.); U.S. Pat. No. 5,438,988 (Duan et al.); and U.S. Pat. No. 5,674,561 (Dietz et al.); as well as International Publication Nos. WO97/24378; WO97/24376; and WO97/24149.

The electrolyte layer 40 may be provided as a preformed layer that is laminated over the undercoating 30. The thickness of the electrolyte layer 40 may vary so long as its electrical characteristics are suitable for use in a biomedical electrode. For example, if provided as a hydrogel pressure sensitive adhesive, the electrolyte layer may have a thickness of, e.g., 100 micrometers to 1.5 millimeters.

It may be preferred that the outer perimeter 46 of the electrolyte layer 40 be located outside the of the outer perimeter 26 of the conductive polymeric sheet 20 and the conductive undercoating 30 on the lower side 22 of the sheet 20. By providing a larger electrolyte layer 40, edge effects associated with current distribution at the outer perimeter 26 of the conductive polymeric sheet 20 and undercoating 30 may be dissipated. The electrolyte layer 40 may also include, e.g., an embedded scrim or other structures/layers to further counter edge effects as described in, e.g., U.S. Pat. No. 6,356,779 (Katzenmaier et al.).

Before use, the biomedical electrode 10 may include a protective cover in the form of, e.g., a release liner 50 that includes an upper surface 54 designed to adhere to, yet easily and cleanly remove from the electrolyte layer 40 when desired. Such release liners will be well known to those of skill in the art and will not be further described herein.

The upper surface 24 of the conductive polymeric sheet 20 is preferably covered with a current spreading layer 60 such that the current spreading layer 60 is coextensive with the upper surface 24 of the conductive polymeric sheet 20. By "coextensive" as used in connection with the present invention, it is meant that the current spreading layer 60 extends substantially to the outer perimeter 26 of the conductive polymeric sheet 20. Alternatively, the outer perimeter of the current spreading layer 60 may be located inward of the perimeter 26 of the conductive polymeric sheet 20 such that the upper surface 24 of the conductive polymeric sheet 20 forms a frame around the current spreading layer 60 that is free of the current spreading layer 60.

The current spreading layer 60 may take the form of any suitably electrically conductive material, e.g., a metallic layer on the conductive polymeric sheet 20. It may be preferred that the contact between the current spreading layer 60 and the upper side 24 of the conductive polymeric sheet 20 be substantially uniform to enhance even distribution of electrical current over the conductive polymeric sheet 10. It may be preferred that the interface between the current spreading layer 60 and the conductive polymeric sheet 20 be substantially free of any intervening adhesive, e.g., pressure sensitive adhesive, hot melt adhesive, epoxy, etc. In such an embodiment, the biomedical electrode may be described as being free of adhesive between the current spreading layer 60 and the conductive polymeric sheet 20. Examples of constructions that are free of any adhesive between the metallic layer of the current spreading layer 60 and the conductive polymeric sheet 20 may include, e.g., electrically conductive inks forming a metallic layer printed onto the conductive polymeric sheet, electroplated metallic layers on the conductive polymeric sheet, vapor-deposited metallic layers on the conductive polymeric sheet, etc.

Another potentially preferred characteristic of the current spreading layer 60 is that the material or materials used for the current spreading layer 60 may preferably exhibit a bulk conductivity that is greater than the bulk conductivity of the materials used to form conductive polymeric sheet 20. In this context, the bulk conductivity of either component is measured in its composite form, i.e., in the case of the conductive polymeric sheet 20, bulk conductivity would be measured of polymeric matrix incorporating electrically conductive particles (if that is the formulation of the conductive polymeric sheet 20 used in the electrode 10). It may be preferred that the bulk conductivity of the material or materials used in the current spreading layer 60 exhibit a bulk conductivity that is two or more (or even five or more) times the bulk conductivity of the materials used to form the conductive polymeric sheet 20.

It is preferred that the result of the relative bulk conductivities of the current spreading layer 60 and the conductive polymeric sheet 20 is that the current spreading layer 60 may exhibit electrical conductivity in the x-y plane (across the upper surface 24 of the conductive polymeric sheet 20) that is greater than the electrical conductivity of the conductive polymeric sheet 20 in the z-direction (i.e., between its upper surface 24 and lower surface 22).

The current spreading layer 60 may preferably include one or more metals (as, e.g., elemental metals, metal alloys, metal salts, etc.). The metal or metals may be supplied in, e.g., inks or paints that include a binder to carry and retain the metal or metals in the current spreading layer 60. In another alternative, the metal or metals may be vapor-deposited on the upper surface 24 of the conductive polymeric sheet 20. Other techniques to provide a current spreading layer 60 may include, but are not limited to laminating a metal foil to the conductive polymeric sheet 20, electroplating the conductive polymeric sheet 20, etc.

It may be preferred that the current spreading layer 60 function as a moisture barrier to significantly reduce or prevent the passage of moisture from, e.g., the conductive adhesive 40, through to the upper surface 64 of the current spreading layer 60. By functioning as a moisture barrier, it is not meant that the current spreading layer 60 necessarily be moisture impermeable. Rather, it may be sufficient that the current spreading layer 60 impede the passage of moisture therethrough.

It may also be preferred that the current spreading layer 60 also act as a barrier to impede the passage of any components of the electrolyte layer 40, especially, e.g., ionic species such as (if present) chloride ions. Such ionic species can rapidly degrade electrical connections by, e.g., increasing resistance.

In some embodiments, the current spreading layer 60 may be provided as a continuous layer that covers all of the upper surface 24 of conductive polymeric sheet 20 (with the exception of pinholes and other minor manufacturing defects that may occur in any process). Alternatively, the current spreading layer 60 may be provided as a patterned current spreading layer.

The patterned current spreading layer includes voids in which the upper surface of any conductive polymeric sheet is free of the current spreading layer, with those voids typically being larger and/or more numerous than any naturally occurring manufacturing defects such as pinholes. Furthermore, the outer perimeter of any patterned current spreading layer may be coextensive with the underlying conductive polymeric sheet or it may be located inward of the perimeter of the conductive polymeric sheet such that the upper surface of the conductive polymeric sheet forms a frame around the current spreading layer that is free of the current spreading layer.

Many patterns may be suitable for use in connection with the current spreading layer in biomedical electrodes of the present invention. Also, although the pattern may be a regular, repeating pattern, the patterns used may be irregular, random, or contain any desired variations, e.g., less density towards the outer edges of the conductive polymeric sheet.

In addition to the characteristics described above, it may be preferred that the current spreading layer be radiolucent such that it does not impede effective radiological imaging of the patient's anatomy underneath the biomedical electrode.

The biomedical electrode depicted in FIG. 1 also includes an electrical connector 70 in the form of a wire that includes multiple electrically conductive strands 72. The strands 72 may preferably be fanned out over a portion of the current spreading layer 60 to assist in distributing the current passing from the strands into the current spreading layer 60 over as large an area as possible.

The strands 72 may be formed of any suitably electrically conductive material or materials. For example, the strands 72 may be metal-coated fibers (e.g., carbon fibers, polymeric fibers, etc.), aluminum strands, copper strands, gold strands, etc. If metal-coated fibers are used, suitable metals may include, e.g., nickel, copper, silver, gold, combinations of one or more metals, etc.

It may be preferred that the electrical connector 70, if provided in the form of a wire as depicted in FIG. 1, also contribute to the radiolucency of the biomedical electrode 10 as a whole. To improve radiolucency, it may be preferred that the strands 72 of the electrical connector 70 be metal-coated carbon fibers or aluminum strands to reduce their shadow in a radiological image.

To further improve radiolucency of the biomedical electrode 10 as a whole, it may further be preferred that any jacket 74 provided to electrically insulate the strands 72 also be constructed of a material or materials that do not cast a significant shadow in a radiological image. It may be preferred that the shadow cast by the jacket 74 in a radiological image be no greater than the shadow cast by the wire bundle located within the jacket 74. Such materials are typically those with lower molecular weights. One example of a suitable material is SANTOPRENE (Advanced Elastomer Systems, L.P., Akron Ohio).

If the electrical connector 70 is provided in the form of a wire as seen in FIG. 1, the strands 72 may be connected to and held in place on the upper surface 64 of the current spreading layer 60 by an electrically conductive adhesive tape 80 located between the strands 72 and the upper surface 64 of the current spreading layer 60. The conductive adhesive tape 80 may be of any suitable design. Examples of suitable conductive pressure sensitive adhesive tapes include, but are not limited to XYZ-AXIS ELECTRICALLY CONDUCTIVE TAPE (No. 9712 or 9713) (3M, St. Paul, Minn.). Other suitable electrically conductive pressure sensitive adhesive tapes may be described in U.S. Pat. No. 5,571,165 (Ferrari).

In addition to a layer of tape 80 between the strands 72 and the upper surface 64 of the current spreading layer 60, it may be desirable to provide for one or more additional layers of an electrically conductive pressure sensitive adhesive tape 85 to be located over the strands 72, such that the strands 72 are located between the two opposing layers 80 and 85 of electrically conductive pressure sensitive adhesive tape.

Potential advantages of using one or both layers of electrically conductive pressure sensitive adhesive tape may include preventing relative movement between the strands 72 and the current spreading layer 60; enclosing the strands 72 to further reduce the likelihood of corrosion; and to provide a low resistance connection between the electrical connector 70 and the current spreading layer 60.

Other techniques of connecting the electrical connector 70 to the current spreading layer 60 may be used in place of or in addition to electrically conductive pressure sensitive adhesive tape. For example, the strands 72 could be attached using a non-conductive adhesive tape placed over the strands 72 (see, e.g., tape 85 in the absence of tape 80 in FIG. 1), forcing the strands 72 into contact with the upper surface 64 of the current spreading layer 60. Alternatively, the strands 72 could be attached to the current spreading layer 60 using a mass of electrically conductive adhesive or epoxy in the absence of a structural backing to carry the adhesive.

In addition to attaching the strands 72 of the electrical connector 70 to the current spreading layer 60, it may also be advantageous, if the electrical connector 70 is provided in the form of a wire, to anchor the electrical connector 70 to the current spreading layer 60 at a location between the exposed strands 72 and the edge 26 of the conductive polymeric sheet 20. In the depicted embodiment, the anchor is provided in the form of an adhesive tape 78, although any suitable technique or combination of techniques may be used to anchor the electrical connector 70. Examples of some additional suitable anchoring techniques include, but are not limited to: two or more anchoring tapes, double-sided adhesive tape, staples, adhesives (e.g., hot melt adhesives, pressure sensitive adhesives, etc.), epoxies, etc. The anchor 78 may be helpful to distribute forces on the electrical connector 70 to the conductive polymeric sheet 20 in areas outside of the electrical connection made at the strands 72.

Additionally, if provided in the form of a wire, the electrical connector 70 may include a kink 76 formed therein to further increase the force required to pull the wire out of the electrode 10.

The depicted medical electrode 10 also includes a backing 90 located over current spreading layer 60, the electrical connector 70 and the conductive tapes 80 and 85. The backing 90 may preferably have a high dielectric strength does not conduct electricity delivered to the electrode 10 through the electrical conductor 70. The backing 90 may be constructed of any suitable material or materials that provide the desired electrical characteristics. Examples of some suitable materials may include, but are not limited to: polymeric films, foam sheets, nonwoven sheets, woven sheets, etc. and combinations of two or more different materials (e.g., a foam and a nonwoven layer).

The backing 90 may preferably include a non-conductive pressure sensitive adhesive 98 on the lower surface 92 of the backing 90, i.e., the surface facing the current spreading layer 60. The pressure sensitive adhesive 98 is preferably located over the entire lower surface 92 of the backing 90 such that the pressure sensitive adhesive 98 can assist in retaining the electrical conductor 70 in place on the electrode 10, as well as provide a unitary electrode construction. Alternatively, however, it may be sufficient that the pressure sensitive adhesive 98 be located over only portions of the backing 90.

It may also be preferred that the backing 90 have an outer perimeter 96 that extends beyond the outer perimeter 26 of the conductive polymeric sheet 20 and the outer perimeter 46 of the conductive adhesive 40 such that the backing 90 and its pressure sensitive adhesive 98 can assist in retaining the medical electrode 10 on the skin of a patient. If desired, the pressure sensitive adhesive 98 may be limited to the area of the lower surface 92 of the backing 90 that extends beyond the outer perimeter 26 of the conductive polymeric sheet 20, or the area of the lower surface 92 of the backing 90 that extends beyond the outer perimeter 46 of the conductive adhesive 40. In either event, if the pressure sensitive adhesive 98 is provided, it will typically be desirable to provide the release liner 50 in a size that is large enough to cover the pressure sensitive adhesive 98 on the backing 90.

Figure 2:
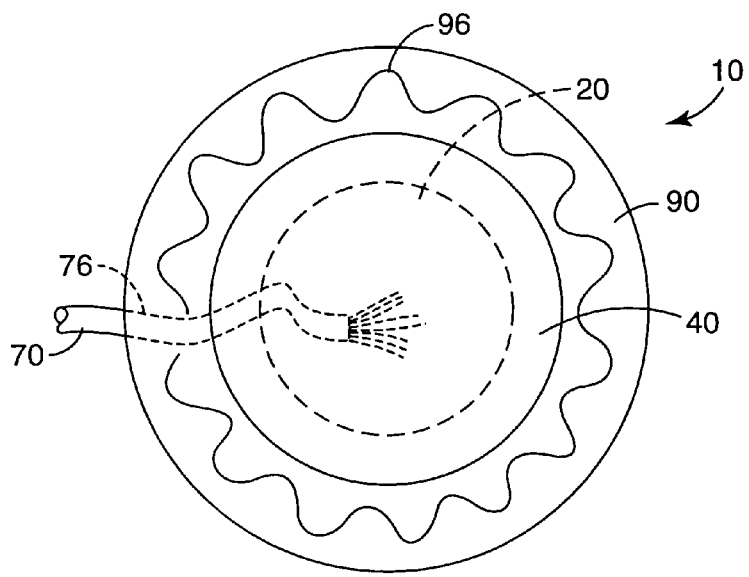
FIG. 2 is a plan view of the bottom surface of the biomedical electrode with the release liner removed to expose the electrolyte layer located thereon.

FIG. 2 is a plan view of the bottom surface of the medical electrode 10 with the release liner 50 removed to expose the conductive adhesive 40. As seen in FIG., 2, the backing layer 90 with its adhesive 98 preferably frames the conductive adhesive 40. Likewise, it may be preferred that the conductive adhesive 40 frames the conductive polymeric sheet 20 (depicted in broken lines) to, as discussed above, disperse current at the edges of the conductive polymeric sheet 20.

Figure 3:
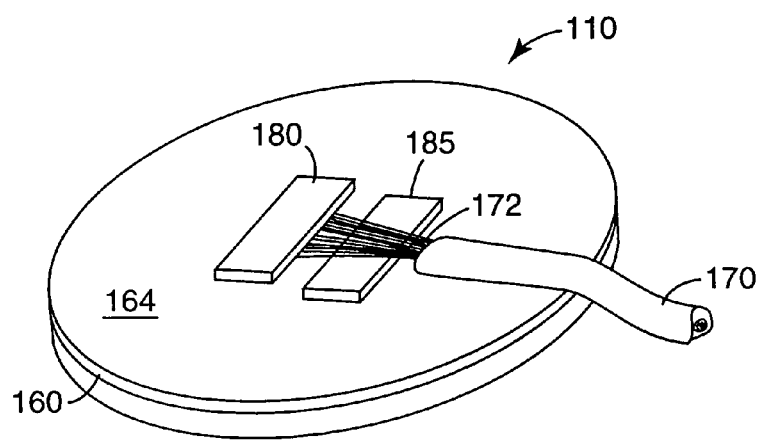
FIG. 3 is a perspective view of another biomedical electrode with the backing removed to expose the electrical conductor and the current spreading layer on the conductive polymeric sheet.

FIG. 3 is a perspective view of an alternative medical electrode 110 according to the present invention without a backing such that the current spreading layer 160 and electrical connector 170 with strands 172 are exposed. The illustrated electrical connector 170 is attached to the current spreading layer 160 in a slightly different manner than that depicted in the medical electrode 10 of FIG. 1. A portion of the strands 172 of the electrical connector 170 are in direct contact with the upper surface 164 of the current spreading layer 160, with a pressure sensitive adhesive tape 180 located over the top of the strands 172 such that the strands 172 are located between the upper surface 164 of the current spreading layer 160 and the tape 180. A second tape 181 may be provided over the strands 172 at the point at which they exit the jacket of connector 170.

In addition to tapes 180 and 181 located over the ends of the strands 172, it may also be advantageous to provide a second tape 185 located between a portion of the strands 172 and the current spreading layer 160. It may be preferred that tape 185 be an electrically conductive pressure sensitive adhesive tape to assist in distributing current over a larger area as it passes from the stands 172 to the current spreading layer 160. The two tapes 180 & 181 may not overlap tape 185 other as seen in FIG. 3 or, alternatively, they may overlap.

All of the illustrative embodiments described above include an electrical connector in the form of a wire with exposed strands. It should, however, be understood that the electrical connectors used in connection with biomedical electrodes of the present invention may take any suitable form. One example may include, e.g., electrically conductive post studs as discussed in U.S. Pat. No. 5,733,324 (Ferrari).

Figure 4:
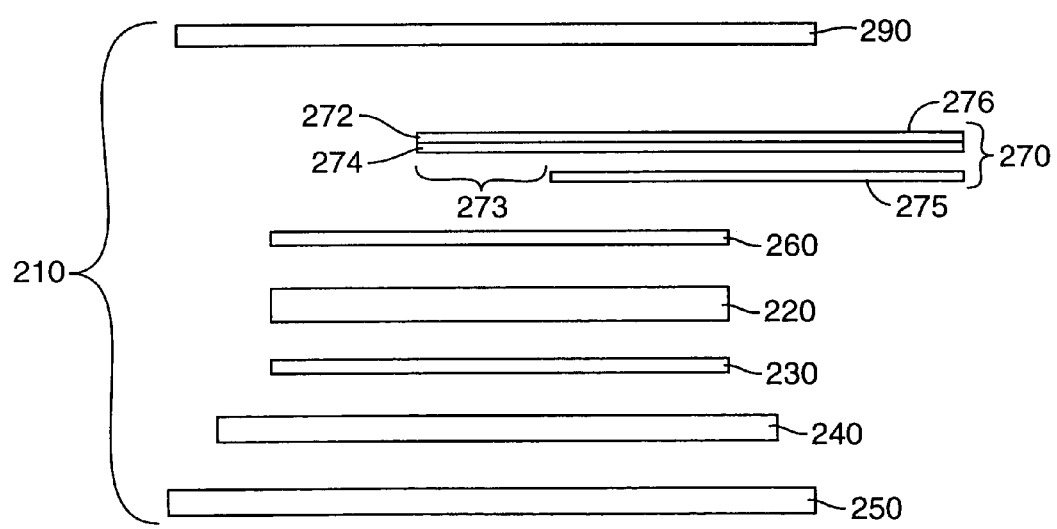
FIG. 4 is an exploded edge view of another medical electrode according to the present invention.

FIG. 4 depicts another alternative electrical connector 270 in connection with medical electrode 210. The electrical connector 270 is provided in the form of a conductive sheet 272 (e.g., metallic foil, metal-coated polymeric film, etc.) with a conductive adhesive 274 attaching the conductive sheet 272 to the current spreading layer 260. The remaining components of the medical electrode such as the conductive polymeric sheet 220, conductive undercoating 230, conductive adhesive 240, release liner 250, and backing 290 may all be substantially as described in the illustrative embodiments presented above.

The electrical connector 270 may preferably include an area 273 in which the conductive adhesive 274 is exposed to make electrical connection with the current spreading layer 260 proximate the central area of the conductive polymeric sheet 220. Similarly, a portion of the conductive sheet 272 may be exposed outside the perimeter of the backing 290 to form a tab 276 to which a connector (e.g., a clamp) can be attached to deliver electrical energy to the electrode 210. The lower surface of the conductive adhesive 274 may be covered by a non-conductive layer 275 such that electrical energy delivered to the current spreading layer 260 through the conductive sheet 272 enters proximate the central area of the current spreading layer 260. The layer 275 may include an adhesive attaching it to the current spreading layer 260.

Figure 5:
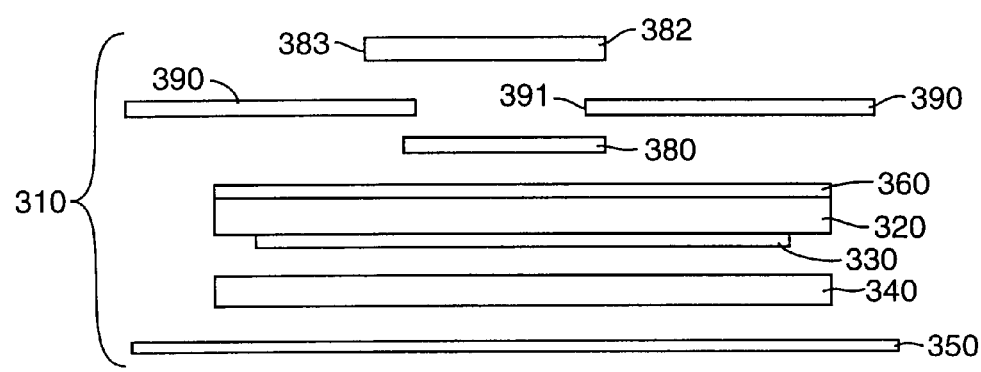
FIG. 5 is an exploded edge view of another biomedical electrode according to the present invention.
Figure 6:
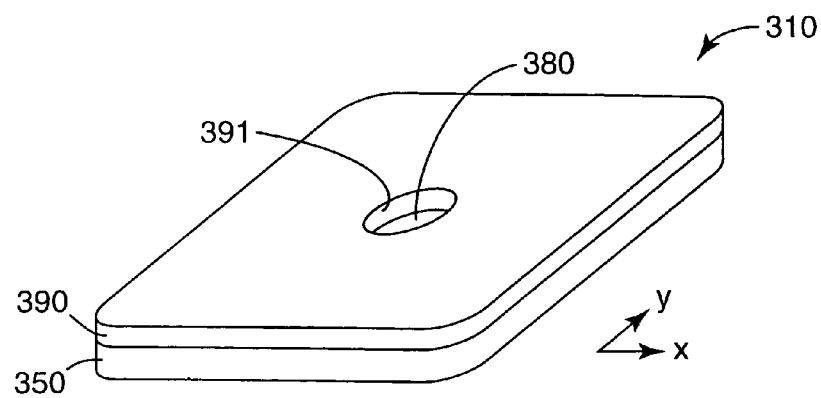
FIG. 6 is a perspective view of the biomedical electrode of FIG. 5 with the connection liner removed.

FIGS. 5 & 6 depict another alternative electrical connection scheme in a biomedical electrode according to the present invention. FIG. 5 is an exploded edge of the biomedical electrode 310. The majority of the components in the biomedical electrode 310 such as the conductive polymeric sheet 320, conductive undercoating 330, electrolyte layer 340, release liner 350, and backing 390 may all be substantially as described in the illustrative embodiments presented above.

Where the electrode 310 differs in how electrical energy is delivered to the electrode 310. In the depicted embodiment, an electrically conductive adhesive tape 380 is attached to the current spreading layer 360 on the conductive polymeric sheet 320. At least a portion of the tape 380 is exposed through a void 391 formed in the backing 390. Before use, the portion of the tape 380 exposed through void 391 may be protected by a release liner 382. The liner 382 may be oversized relative to opening 391 to provide an edge 383 that may be easily grasped when liner 382 is to be removed.

In another variation, electrically conductive tape 380 may not be provided with a portion of the current spreading layer 360 exposed through void 391. In such an embodiment, liner 382 may be replaced by, e.g., an adhesive tape that could be used to retain an electrical conductor (not shown) in contact with the current spreading layer 360 such that electrical energy can pass between the connector and the current spreading layer 360.

Although the opening 391 and tape 380 are shown as being located proximate a center of the electrode 310, the location may be vary, including to locations along the edge of the electrode 310 if the tape 380 is attached to the current spreading layer 360 to disperse the electrical energy over the x-y plane of the electrode 310.

EXAMPLES

The following nonlimiting examples are presented to further understanding of the present invention.

Example 1

A conductive polymeric sheet with a thick silver ink layer coated on one side was obtained from Prime Label Inc. (Pewaukee, Wis.). The conductive polymeric sheet was made of PVC rendered electrically conductive by inclusion of carbon powder. The silver ink layer formed the current spreading layer of the electrode.

The opposite surface of the conductive polymeric sheet, i.e., the surface that was not coated with the silver ink forming the current spreading layer, was coated with an approximately 10 micrometer thick layer of silver-silver chloride ink (R301 available from Ercon Inc., Wareham, Mass.). The silver-silver chloride ink layer formed the conductive undercoating on the conductive polymeric sheet.

Pieces were cut out of the sheet with the current spreading layer and the conductive undercoating in rectangular shapes having sides with lengths of approximately 11 centimeters (cm) by 7 cm.

A hydrogel electrolyte adhesive with a thickness of 0.5 millimeters was laminated to the silver-silver chloride layer on the conductive polymeric sheet. The outer perimeter of the hydrogel electrolyte adhesive extended beyond the edge of the conductive polymeric sheet. The hydrogel electrolyte adhesive was made using the procedures described in U.S. Pat. No. 4,848,353 (Engel). The composition of the hydrogel electrolyte adhesive was as follows:

| Constituent | Weight % |
| --- | --- |
| Acrylic Acid | 20.6 |
| Glycerine | 25.0 |
| Sodium Hydroxide (50% Solution) | 17.85 |
| Water | 30.3 |
| IRGACURE 2959 | 0.1 |
| IRGACURE 651 | 0.05 |
| Methylene bis acrylamide | 0.04 |
| Guar Gum | 0.10 |
| Xylitol | 2.0 |
| Potassium Chloride | 4.0 |

A 2.5 cm by 2.5 cm piece of electrically conductive pressure sensitive adhesive tape (Product No. 9712 or 9713 from 3M of St. Paul Minn.) was adhered to the silver ink current spreading layer on the conductive polymeric sheet. The tape was adhered within the center of the conductive polymeric sheet.

An electrical connector in the form of a wire was connected to the electrode. The wire was obtained from Minnesota Wire and Cable (St. Paul, Minn.) and included 12,000 nickel-copper coated fine strands in a bundle diameter of approximately 0.9 mm and insulating jacket diameter of 2.2 mm. Approximately 1.5–2 cm of the insulating jacket was removed from the end of the wire to expose the strands. The strands were fanned out and adhered to the pressure sensitive adhesive tape on the silver ink current spreading layer. A second piece of the electrically conductive pressure sensitive adhesive tape was applied over the strands to retain and cover them.

The electrical connector was further anchored to the electrode using a piece of pressure sensitive adhesive tape placed over the insulating jacket at a location between the electrically conductive pressure sensitive adhesive tapes and the edge of the conductive polymeric sheet.

A backing was then laminated over the current spreading layer and the electrical connector mounted thereon. The backing was in the form of a sheet of non-conductive foam with a non-conductive pressure sensitive adhesive on one side (marketed as VOLARA by Voltek Inc., Mass.). The backing was larger than the conductive polymeric sheet such that the perimeter of the backing extended beyond the perimeter of the conductive polymeric sheet and the hydrogel electrolyte adhesive.

Pairs of electrodes manufactured as described above were attached to each other using their hydrogel electrolyte adhesive layers. The mated pairs of electrodes were then subjected to simulated defibrillation tests by connecting the electrodes to a circuit containing a 50 ohm resistor and a 1 ohm resistor. The voltage across the resistors was measured on an oscilloscope (Hewlett Packard Model 54601 A).

The defibrillator used was a LIFE PAK 9 (Physio Control Inc. of Redmond, Wash.). Increasing energy settings were utilized as shown below, with three defibrillation pulses delivered at each energy setting at an interval of about 10–20 seconds between pulses. The ratio of the peak voltage to the resistor value was used to calculate the current through the electrode and, thus, through the connector. The ratio of the peak voltage to the current gives the resistance of the mated electrode pair.

Table 1 includes data using electrodes constructed with 3M 9712 electrically conductive pressure sensitive adhesive tape manufactured with carbon fiber strands. Table 2 includes data using mated electrode pairs constructed with 3M 9713 electrically conductive pressure sensitive adhesive tape manufactured with nickel coated carbon fiber strands. Note that each value for current, voltage and resistance in the tables is the average of three defibrillator pulses at each energy level.

TABLE 1

| Pulse Energy (J) | Current (a) | Voltage (v) | Resistance (ohms) |
|---|---|---|---|
| 100 | 20.3 | 109 | 5.4 |
| 200 | 33.3 | 157 | 4.7 |
| 360 | 46.9 | 196 | 4.2 |

TABLE 2

| Pulse Energy (J) | Current (a) | Voltage (v) | Resistance (ohms) |
|---|---|---|---|
| 100 | 23.4 | 149 | 6.4 |
| 200 | 34.4 | 206 | 6.0 |
| 360 | 46.9 | 254 | 5.4 |

Both samples exhibited acceptable performance, with resistance decreasing during use. It is theorized that a conductive adhesive tape with higher conductivity would provide even lower resistance values.

All references and publications cited herein are expressly incorporated herein by reference in their entirety into this disclosure. Illustrative embodiments of this invention are discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

The invention claimed is:

1. A biomedical electrode comprising:
    a conductive polymeric sheet comprising an upper side and a lower side;
    a conductive undercoating attached to the lower side of the conductive polymeric sheet;
    an electrolyte layer attached to the conductive undercoating, wherein the conductive undercoating is located between the electrolyte layer and the lower side of the conductive polymeric sheet;
    a current spreading layer attached to the upper side of the conductive polymeric sheet, wherein the current spreading layer comprises a metallic layer on the upper side of the conductive polymeric sheet, and wherein the biomedical electrode is free of adhesive between the metallic layer and the conductive polymeric sheet; and
    an electrical connector attached to the biomedical electrode, the electrical connector in electrical communication with the conductive polymeric sheet through the current spreading layer.

2. A biomedical electrode according to claim 1, wherein the metallic layer exhibits a bulk conductivity that is greater than a bulk conductivity of the conductive polymeric sheet.

3. A biomedical electrode according to claim 1, wherein the metallic layer consists essentially of one or more metals.

4. A biomedical electrode according to claim 1, wherein the metallic layer comprises an electrically conductive ink.

5. A biomedical electrode according to claim 1, wherein the current spreading layer is coextensive with the upper side of the conductive polymeric sheet.

6. A biomedical electrode according to claim 1, wherein the current spreading layer comprises a pattern that comprises one or more voids, wherein a portion of the upper side of the conductive polymeric sheet is free of the metallic layer within the one or more voids.

7. A biomedical electrode according to claim 1, wherein the current spreading layer comprises a moisture barrier between the electrical connector and the electrolyte layer.

8. A biomedical electrode according to claim 1, wherein the conductive undercoating comprises a substantially non-polarizable interface with the electrolyte layer.

9. A biomedical electrode according to claim 1, wherein the conductive polymeric sheet comprises electrically conductive particles dispersed in a polymeric matrix.

10. A biomedical electrode according to claim 1, wherein the electrolyte layer comprises ionically conductive hydrogel pressure sensitive adhesive.

11. A biomedical electrode according to claim 1, further comprising on electrically conductive adhesive tape, wherein the electrically conductive adhesive tape attaches the electrical connector to the current spreading layer.

12. A biomedical electrode according to claim 11, wherein at least a portion of the electrically conductive adhesive tape is located between the electrical connector and the current spreading layer.

13. A biomedical electrode comprising:
    a conductive polymeric sheet comprising an upper side and a lower side;
    a conductive undercoating attached to the lower side of the conductive polymeric sheet;
    an electrolyte layer attached to the conductive undercoating, wherein the conductive undercoating is located between the electrolyte layer and the lower side of the conductive polymeric sheet;
    a current spreading layer attached to the upper side of the conductive polymeric sheet, wherein the current spreading layer comprises a pattern that comprises one or more voids, wherein a portion of the upper side of the conductive polymeric sheet is free of the current spreading layer within the one or more voids, and wherein the biomedical electrode is free of adhesive between the current spreading layer and the conductive polymeric sheet; and an electrical connector attached to the biomedical electrode, the electrical connector in electrical communication with the conductive polymeric sheet through the current spreading layer.

14. A biomedical electrode according to claim 13, wherein the current spreading layer exhibits a bulk conductivity that is greater than a bulk conductivity of the conductive polymeric sheet.

15. A biomedical electrode according to claim 13, wherein the current spreading layer is coextensive with the upper side of the conductive polymeric sheet.

16. A biomedical electrode according to claim 13, wherein the current spreading layer consists essentially of one or more metals.

17. A biomedical electrode according to claim 13, wherein the current spreading layer comprises an electrically conductive ink.

18. A biomedical electrode according to claim 13, wherein the conductive undercoating comprises a substantially non-polarizable interface with the electrolyte layer.

19. A biomedical electrode according to claim 13, wherein the conductive polymeric sheet comprises electrically conductive particles dispersed in a polymeric matrix.

20. A biomedical electrode according to claim 13, wherein the electrolyte layer comprises ionically conductive hydrogel pressure sensitive adhesive.

21. A method of manufacturing a biomedical electrode, the method comprising:

providing a conductive polymeric sheet comprising an upper side and a lower side;

attaching a conductive undercoating to a lower side of a conductive polymeric sheet;

attaching an electrolyte layer to the conductive undercoating, wherein the conductive undercoating is located between the electrolyte layer and the lower side of the conductive polymeric sheet;

providing a current spreading layer on the upper side of the conductive polymeric sheet, wherein the current spreading layer comprises a metallic layer on the upper side of the conductive polymeric sheet, and wherein the biomedical electrode is free of adhesive between the metallic layer and the conductive polymeric sheet; and attaching an electrical connector to the biomedical electrode, the electrical connector in electrical communication with the conductive polymeric sheet through the current spreading layer.

22. A method according to claim 21, wherein the metallic layer exhibits a bulk conductivity that is greater than a bulk conductivity of the conductive polymeric sheet.

23. A method according to claim 21, wherein the metallic layer consists essentially of one or more metals.

24. A method according to claim 21, wherein the metallic layer comprises an electrically conductive ink.

25. A method according to claim 21, wherein the current spreading layer is coextensive with the upper side of the conductive polymeric sheet.

26. A method according to claim 21, wherein the current spreading layer comprises a pattern that comprises one or more voids, wherein a portion of the upper side of the conductive polymeric sheet is free of the metallic layer within the one or more voids.

27. A method of manufacturing a biomedical electrode, the method comprising:

providing a conductive polymeric sheet comprising an upper side and a lower side;

attaching a conductive undercoating to a lower side of a conductive polymeric sheet;

attaching an electrolyte layer to the conductive undercoating, wherein the conductive undercoating is located between the electrolyte layer and the lower side of the conductive polymeric sheet;

providing a current spreading layer on an upper side of the conductive polymeric sheet, wherein the current spreading layer comprises a pattern that comprises one or more voids, wherein a portion of the upper side of the conductive polymeric sheet is free of the current spreading layer within the one or more voids, and wherein the biomedical electrode is free of adhesive between the current spreading layer and the conductive polymeric sheet; and attaching an electrical connector to the biomedical electrode, the electrical connector in electrical communication with the conductive polymeric sheet through the current spreading layer.

28. A method according to claim 27, wherein the current spreading layer exhibits a bulk conductivity that is greater than a bulk conductivity of the conductive polymeric sheet.

29. A method according to claim 27, wherein the current spreading layer consists essentially of one or more metals.

30. A method according to claim 27, wherein the current spreading layer comprises an electrically conductive ink.

31. A method according to claim 27, wherein the current spreading layer is coextensive with the upper side of the conductive polymeric sheet.

* * * * *

UNITED STATES PATENT AND TRADEMARK OFFICE
CERTIFICATE OF CORRECTION

PATENT NO.       : 7,187,985 B2  
APPLICATION NO.  : 10/623359  
DATED            : March 6, 2007  
INVENTOR(S)      : Hatim M. Carim It is certified that error appears in the above-identified patent and that said Letters Patent is hereby corrected as shown below:

Column 8
Line 1, After "surface" insert -- 60 may be provided as a continuous layer that covers all of the upper surface --.

Column 14
Line 46, In Claim 11, delete "on" and insert -- an --, therefor.

Signed and Sealed this

Fourteenth Day of August, 2007

JON W. DUDAS  
*Director of the United States Patent and Trademark Office*